United States Patent [19]
Watanbe et al.

[11] Patent Number: 5,357,443
[45] Date of Patent: Oct. 18, 1994

[54] METHOD OF ESTIMATING PROPERTIES OF STEEL PRODUCT

[75] Inventors: Yoshiyuki Watanbe; Shinichi Shimomura, both of Kimitsu; Atsuhiko Yoshie; Masaaki Fujioka, both of Futsu; Kiyoshi Nishioka, Kimitsu; Satoshi Akamatsu; Takashi Fujita, both of Futsu, all of Japan

[73] Assignee: Nippon Steel Corporation, Tokyo, Japan

[21] Appl. No.: 978,703

[22] PCT Filed: Jun. 4, 1992

[86] PCT No.: PCT/JP92/00720

§ 371 Date: Feb. 3, 1993

§ 102(e) Date: Feb. 3, 1993

[87] PCT Pub. No.: WO92/21970

PCT Pub. Date: Oct. 12, 1992

[30] Foreign Application Priority Data

Jun. 4, 1991 [JP] Japan ................... 3-159410
Jun. 4, 1991 [JP] Japan ................... 3-159411
Jul. 25, 1991 [JP] Japan ................... 3-207163
Jul. 25, 1991 [JP] Japan ................... 3-207165
Sep. 12, 1991 [JP] Japan ................... 3-260469
Nov. 21, 1991 [JP] Japan ................... 3-331621

[51] Int. Cl.$^5$ ................... G06F 15/46; B22D 11/16
[52] U.S. Cl. ................... 364/472; 148/541; 164/4.1; 164/418
[58] Field of Search ................... 364/472, 551.01, 552; 164/4.1, 452, 418; 148/538, 541, 645, 648

[56] References Cited

U.S. PATENT DOCUMENTS 4,840,051  6/1989  Boratto et al. ................... 72/11

OTHER PUBLICATIONS

ISIJ International, vol. 32, No. 3, (1992) Atsuhiko Yoshie et al., "Modelling of Microstructural Evolution and Mechanical Properties of Steel Plates Produced by Thermo-Mechanical Control Process", pp. 395–404.
Sumitomo Metal, vol. 42, No. 4, (1990) Nozomu Komatsubara and others "Quality Estimation Control Technology for Plank Hot-rolled Steel Plate", pp. 104–112.

(List continued on next page.)

*Primary Examiner*—Paul Gordon
*Attorney, Agent, or Firm*—Kenyon & Kenyon

[57] ABSTRACT

A method of estimating the properties of a steel product, comprising completing a computation for determining metallurgical phenomena based on information concerning steel ingredients and production conditions in steps from casting to heat treatment to successively determine the state of a metallic structure and estimating the properties of a steel product from the final state of the metallic structure. More specifically, the method comprises the steps of: computing the temperature of a slab based on casting conditions and further completing a computation for the state of the metallic structure after casting based on information concerning the temperature of the slab and steel ingredients; completing a computation for the state of the metallic structure after rolling based on the state of the metallic structure before the rolling and the temperature of the steel product computed from rolling conditions; completing a computation for the state of the metallic structure after cooling based on the state of the metallic structure before the cooling and the temperature of the steel product computed from cooling conditions; and completing a computation for the properties of the steel product based on the final state of the metallic structure. In order to cope with the provision of additional production steps such as reheating, a homogeneous diffusion heat treatment, preliminary rolling, quenching, tempering and normalizing, etc., the method may further comprise the steps of completing a computation for the state of the metallic structure after applying the additional steps based on the state of the metallic structure before applying the additional steps and the conditions for the additional steps.

11 Claims, 10 Drawing Sheets

OTHER PUBLICATIONS

Iron and Steel, vol. 75, No. 6, (1989) Satoshi Akamatsu and others "Development of NbC Deposition Model during Hot Working of Austenite Region in Low-carbon Nb Steel", pp. 933–940.

Proc. Int. Conf. on Physical Metsllurgy of Thermo-mechanical Processing of Steels and other Metals, (1988) ed by I. Tamura, ISIJ. Tokyo, A. Yoshie et al. "Estimation Model for Evolution of Microstructure and Mechanical Properties of Nb Bearing Steel Plates Produced by Thermo-Mechanical Control Process", pp. 799–806 No date.

Iron and Steel, vol. 70, No. 15, (1984) Takehide Senuma and others "Changes in Carbon-steel Austenite Texture during High-speed Continuous Hot Working", pp. 2112–2119.

METHOD OF ESTIMATING PROPERTIES OF STEEL PRODUCT

TECHNICAL FIELD

The present invention relates to a method of estimating the properties of a steel product which enables the structure and properties of the steel product to be estimated without conducting a breaking test during or after the production of the steel product.

BACKGROUND ART

For example, users of steel plates etc. often demand of the manufacturer the attachment of the results of a material test concurrently with the delivery of the product. In response to this demand, the manufacturer has hitherto cut out a part of the product and conducted a test of the physical properties (tensile strength, toughness, etc.) of the extracted sample.

In some cases, the properties of the steel product have been estimated based on production conditions such as steel ingredients and rolling termination temperature. Since, however, this is usually done using a regression method and does not take metallurgical phenomenon into consideration, the scope of application is limited and disadvantageously this method cannot be applied to different production processes or steel plate thicknesses.

The above-described artificial measurement of properties requires a lot of time, which influences the shipment and delivery of the product. Further, at the present time, the properties thereof can be discerned only in a finished product, and the development of a technique that enables the properties of the steel product to be estimated before production thereof and, at the same time, provides production conditions capable of providing a high quality goods consistently, is required in the art.

Accordingly, an object of the present invention is to provide a method of estimating the properties of a steel product that enables the properties of the steel product to be automatically assessed based on given production conditions.

DISCLOSURE OF THE INVENTION

In the present invention, in order to attain the above-described object, a computation for metallurgical phenomena is computed based on information concerning steel ingredients and production conditions during the casting to heat treatment steps to successively determine the state of a metallic structure, and the properties of a steel product is estimated from the final state of the metallic structure.

Specifically, the method of estimating the properties of a steel product according to the present invention comprises the steps of: computing the temperature of a slab based on casting conditions and completing a computation for the state of the metallic structure after casting based on information concerning the temperature of the slab and the steel ingredients; completing a computation for the state of the metallic structure after rolling based on the state of the metallic structure before rolling and the temperature of the steel product computed from rolling conditions; completing a computation for the state of the metallic structure after cooling based on the state of the metallic structure before cooling and the temperature of the steel product computed from cooling conditions; and completing a computation for the quality of the steel product based on the final state of the metallic structure.

In order to cope with the provision of additional production steps such as reheating, a homogeneous diffusion heat treatment, preliminary rolling, quenching, tempering and normalizing, etc., the method may further comprise the step of completing a computation for the state of the metallic structure following the additional steps based on the state of the metallic structure before the additional steps and the conditions of the additional steps.

Further, instead of completing a computation for the state of the metallic structure after casting, the state of the metallic structure after casting may be assumed and taken as an initial state.

According to the above-described means, the input of actual results of the production of a steel product or conditions set before the production of the steel product followed by a computation enables a fraction of a phase constituting the structure as the key to the quality of the steel product (tensile strength, toughness, etc.), the amount of formation, grain diameter and state of solid solution and precipitation of the phase at each temperature, etc. to be determined at any stage in the production process, which enables the properties of the steel product to be estimated during production thereof. Further, it becomes possible to set production conditions that can assuredly realize the quality specifications of the steel product. Thus, as opposed to the conventional method, testing and measurement of the finished product can be significantly reduced or eliminated.

BEST MODE FOR CARRYING OUT THE INVENTION

An embodiment of the present invention will now be described taking the production of a steel plate as an example.

Figure 1:
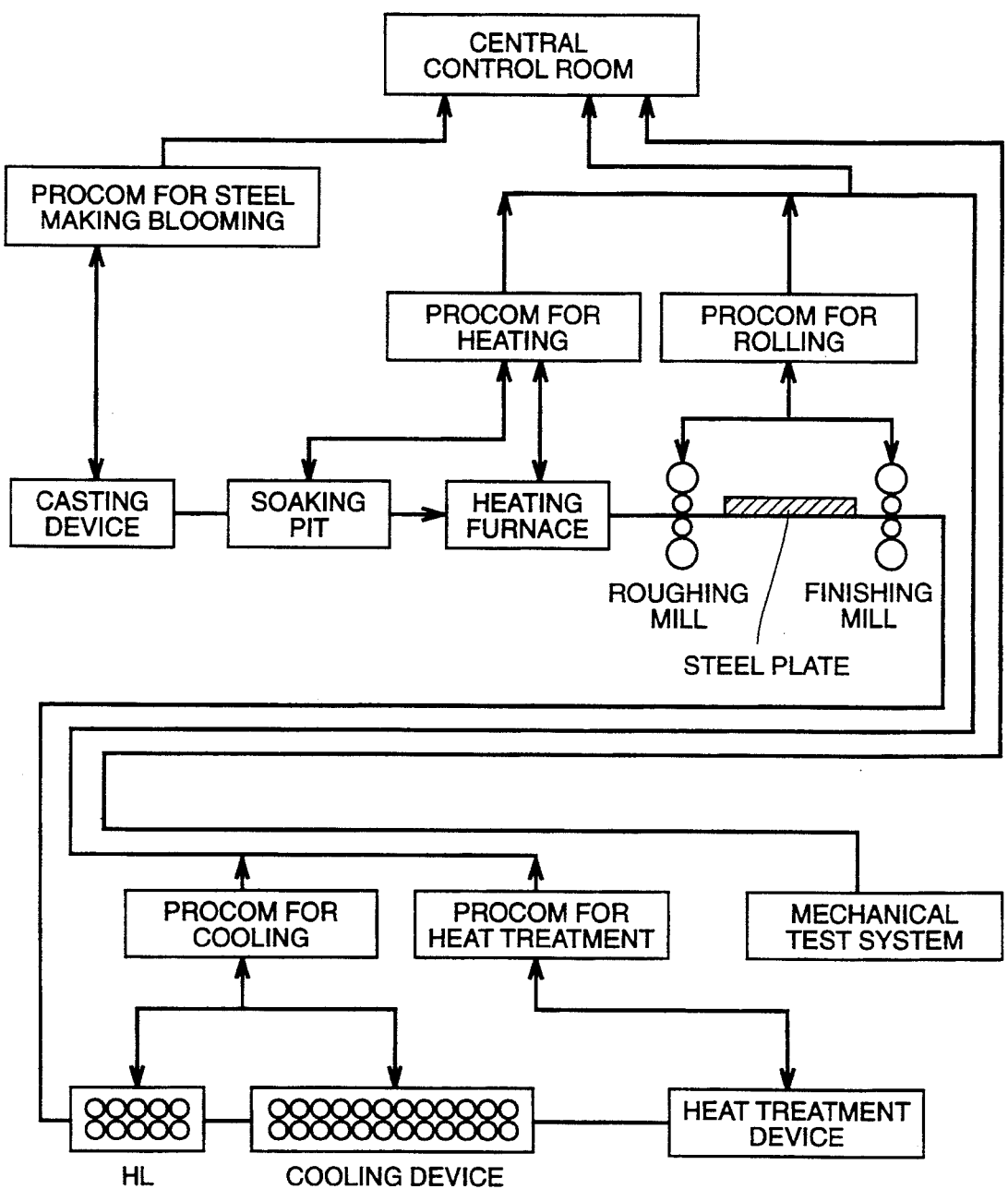
FIG. 1 is a block flow diagram of equipment showing the outline of a steel product production line to which the present invention is applied.

FIG. 1 is a block flow diagram of equipment showing the outline of a steel product production line to which the present invention is applied.

As shown in FIG. 1, the process is roughly classified into a steelmaking step and a steel plate production step. The steelmaking step is divided into refining and casting (solidification). The present invention is directed to steps after casting. Although there is no universal method of classifying the steel plate production step, in the present invention, the steel plate production step is classified into a slab. treatment (a homogeneous diffusion heat treatment or preliminary rolling), reheating, rolling, cooling and a heat treatment (quenching, tempering or normalizing).

The slab cast in the casting equipment (continuous casting or ingot making equipment) is carried to a plate mill which comprises a soaking pit for subjecting the slab to a homogeneous diffusion heat treatment, a heating furnace for heating the slab before rolling, a roughing mill for conducting rough rolling, a finishing mill for rolling the roughly rolled steel plate to a necessary plate thickness, a hot leveler (HL) for correcting the warpage in the steel plate caused by the finishing mill, a cooling device for cooling the steel plate withdrawn from the hot leveler and a heat treatment device for heat-treating the steel plate. The heat treatment device comprises a heating furnace and a cooling device for quenching.

Process computers (hereinafter referred to as "PROCOM") (PROCOM for steel making blooming, PROCOM for heating, PROCOM for rolling, PROCOM for cooling and PROCOM for a heat treatment) are connected to respective equipment and devices for the purpose of driving and controlling the equipment and devices. These PROCOM's are connected to a host computer (not shown) provided in a central control room, and the host computer controls each PROCOM according to production planning. Further, a mechanical test system is provided for a steel plate product for the purpose of conducting a material test. The test results are sent to the central control room.

The method of estimating the properties of the steel product according to the present invention roughly comprises 11 fundamental models, that is, the following models corresponding to respective production steps of the steel product a casting model (a casting step), a homogeneous diffusion heat treatment model (a homogeneous diffusion heat treatment step), a preliminary rolling model (a preliminary rolling step), a heating model (a reheating step), a hot rolling model (a rolling step), a transformation model (a cooling step), a quenching model (a quenching step), a tempering model (a tempering step) and a normalizing step (a normalizing step);

a precipitation model for completing a computation for the state of solid solution and precipitation of elements in each step; and a structure-property model for completing a computation for the mechanical properties of the steel product based on the results of the computation.

In any model, the calculation for the metallurgical phenomena in the step is successively performed so as to complete a computation for the state of the metallic structure. In order for a model to be accessed according to the steps through which the steel product passes, and a computation is completed to automatically estimate the state of the metallic structure and the properties of the final steel product, software is prepared and loaded into the computer.

The construction and computation of each model will now be described in detail.

In the production of a steel plate, the most fundamental production flow comprises casting-reheating of slab-rolling-cooling. Accordingly, at the outset, models corresponding to the fundamental flow will be described.

All the models comprise formulae representing metallurgical phenomena in respective steps, such as growth of grain, recovery, recrystallization and transformation. Many studies have hitherto been completed on the method of describing individual metallurgical phenomena, and the formulae including the following formulae constituting a precipitation model and a structure-property model are reported in, for example, ISIJ International Vol. 32 (1992), No. 3, p. 395.

Figure 2:
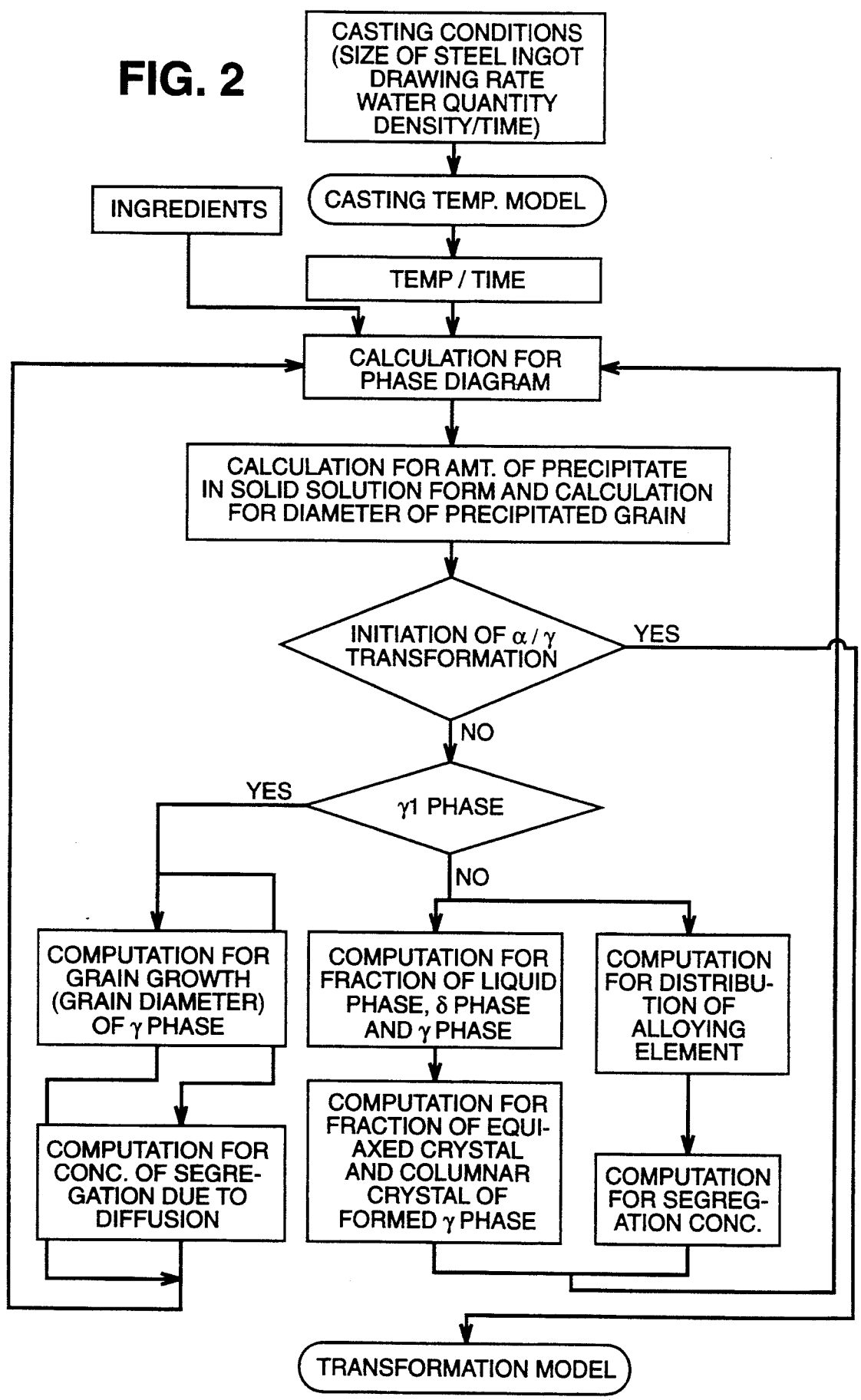
FIG. 2 is a diagram showing a construction and a computing flow of a casting model.

FIG. 2 is a diagram showing a construction and a computing flow of a casting model.

In this model, information concerning steel ingredients and casting conditions are input. The ingredients are expressed in terms of % by weight and carbon (C), silicon (Si), manganese (Mn), phosphorus (P), sulfur (S), copper (Cu), nickel (Ni), chromium (Cr), molybdenum (Mo), niobium (Nb), vanadium (V), titanium (Ti), tantalum (Ta), aluminum (Al), boron (B), tungsten (W), cobalt (Co), calcium (Ca), rare earth elements (Rem), nitrogen (N) and oxygen (O), etc. The information concerning casting conditions includes slab thickness, drawing rate, cooling water quantity density and elapsed time after drawing in the case of a continuous casting process, and steel ingot size in the case of an ingot making process.

In the computation step, at the outset, the thermal history is calculated using a casting temperature model based on casting conditions. The calculation for a phase diagram is then performed based on the information concerning steel ingredients. As is well known in the art, since the crystalline structure varies (transforms) depending upon temperature, the temperature calculated at given elapsed time intervals is checked against a phase diagram to determine whether or not the $\gamma/\alpha$ transformation has been initiated. If the $\gamma/\alpha$ transformation has not been initiated, it is determined whether or not the temperature has lowered to such an extent that the $\gamma$-phase forms. If the judgment is negative, the fractions of the liquid phase, $\delta$ phase and $\gamma$-phase are calculated, and with respect to the $\gamma$-phase, the fractions of an equi-axed crystal and a columnar crystal are calculated. Further, the distribution of the alloying elements between phases is calculated to determine the segregation concentration. This calculation is repeated until the temperature necessary for forming the $\gamma$-phase is attained. When it is determined that the temperature is below the $\gamma$-phase formation temperature, the grain growth in terms of $\gamma$-grain diameter and the change in segregation concentration owing to diffusion of the alloying elements are calculated. On the other hand, when it is determined that the temperature has lowered to the $\gamma/\alpha$ transformation initiation temperature, the model is transferred to a transformation model, which will be described later.

The computation flow shown in FIG. 2 is not limited to the case where the computation is performed to the final step, and when the transfer to the next step has been conducted during the process, that is, when rolling (straightforward rolling) or insertion into the heating furnace (hot charge rolling) has been effected, the state of the metallic structure at that time is transferred to a model corresponding to the next step.

Figure 3:
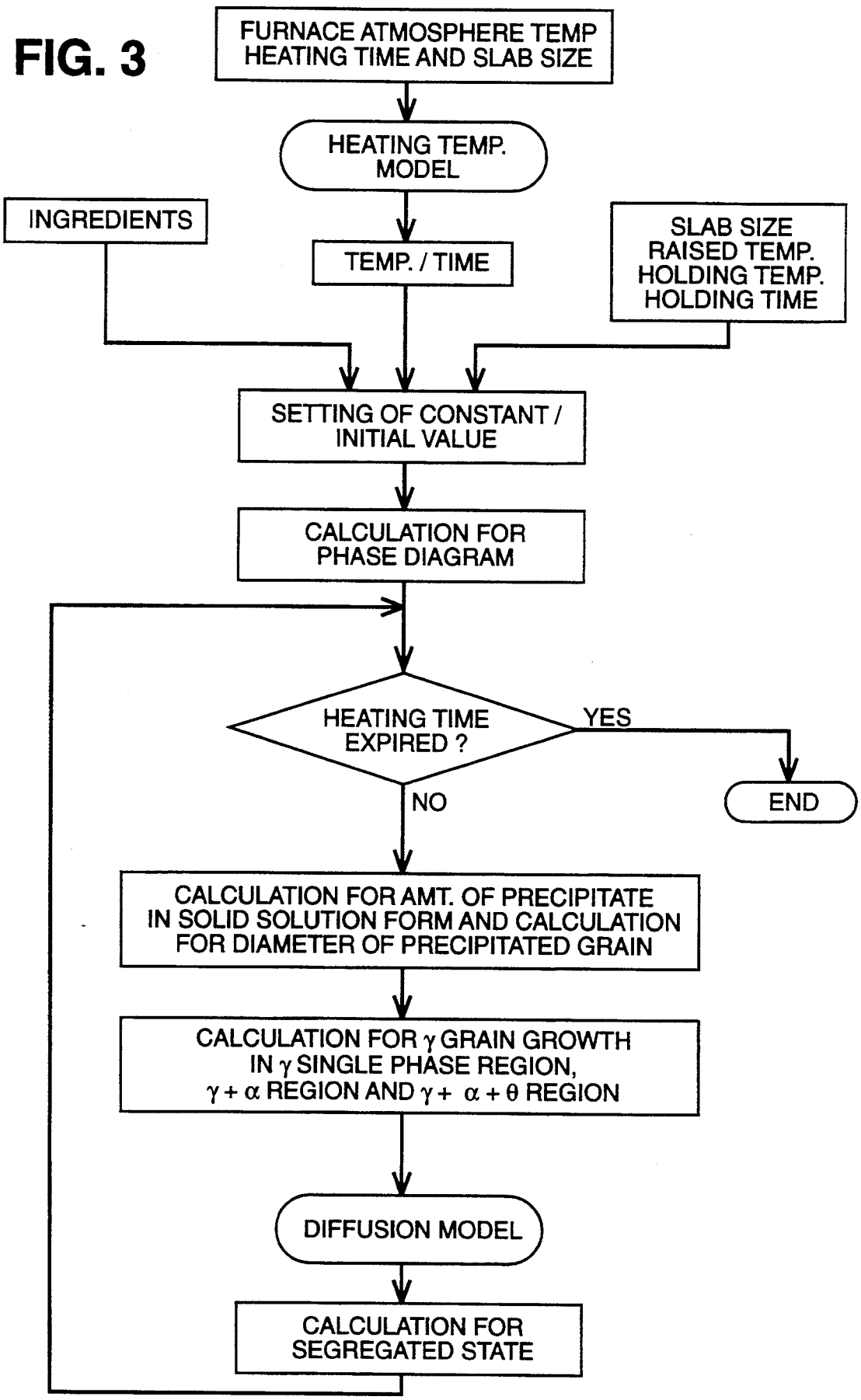
FIG. 3 is a diagram showing a construction and a computing flow of a heating model.

FIG. 3 is a diagram showing a construction and a computing flow of a heating model.

In this model, the results of a computation of a model corresponding to the previous step (for example, casting) or information concerning a previous structure arbitrarily set without computation, information concerning a slab, such as ingredients and size, and heating conditions are input. The furnace atmosphere temperature and the period of time in the furnace or the temperature rise rate and the holding temperature/time can be input as heating conditions. It is possible to input actual conditions as well as virtual heating conditions.

In the computation step, the thermal history is computed based on slab size and heating conditions using a heating temperature model. The calculation for a phase diagram is then performed based on information concerning steel ingredients.

As is well known in the art, since the crystal structure of steel varies (transforms) depending upon temperature, the state of the heated structure (austenite grain diameter) is computed using different techniques for each state. Specifically, if necessary, the temperature computed at given elapsed time intervals is checked against a phase diagram so as to perform a calculation for the growth of austenite grains in a region of austenite+ferrite+cementite, a region of austenite+ferrite and a single region of austenite. At that time, a precipitation model, which will be described later, is computed parallel with the calculation for grain growth so as to add the state of solid solution and precipitation of each element during heating to the computing conditions of the heated structure (austenite grain diameter).

Further, in a single phase region of austenite, a change in the state of segregation is computed using a diffusion model based on the results of a computation of the above-described thermal history.

Figure 4:
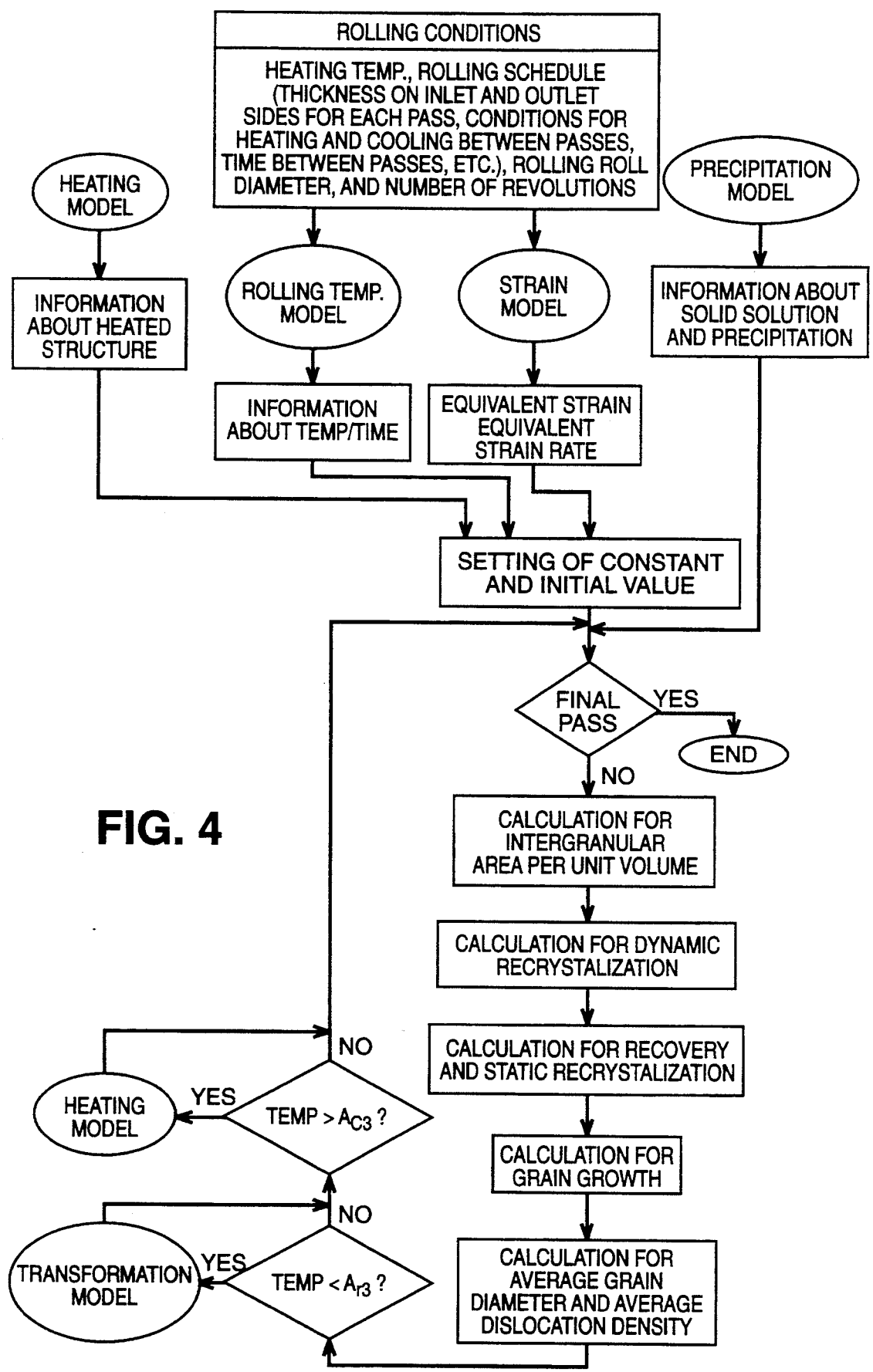
FIG. 4 is a diagram showing a construction and a computing flow of a hot rolling model.

FIG. 4 is a diagram showing a construction and a computing flow of a hot rolling model.

In this model, information concerning a slab, such as ingredients and size, the results of a computation of the model in the previous step or arbitrarily assumed conditions corresponding to the model and rolling conditions, are input. In the case of straightforward rolling, the previous step comprises casting, while in other cases, it usually comprises the reheating of a slab. The rolling conditions include a steel product thickness on inlet and outlet sides, the period of time between passes, the roll diameter and the number of roll revolutions.

In the computation step, at the outset, the thermal history is computed from a rolling temperature model based on the input items, and corresponding strain/equivalent strain rate distribution is computed from a strain model. In the temperature calculation, the removal of heat and other parameters are also taken into consideration.

Figure 5:
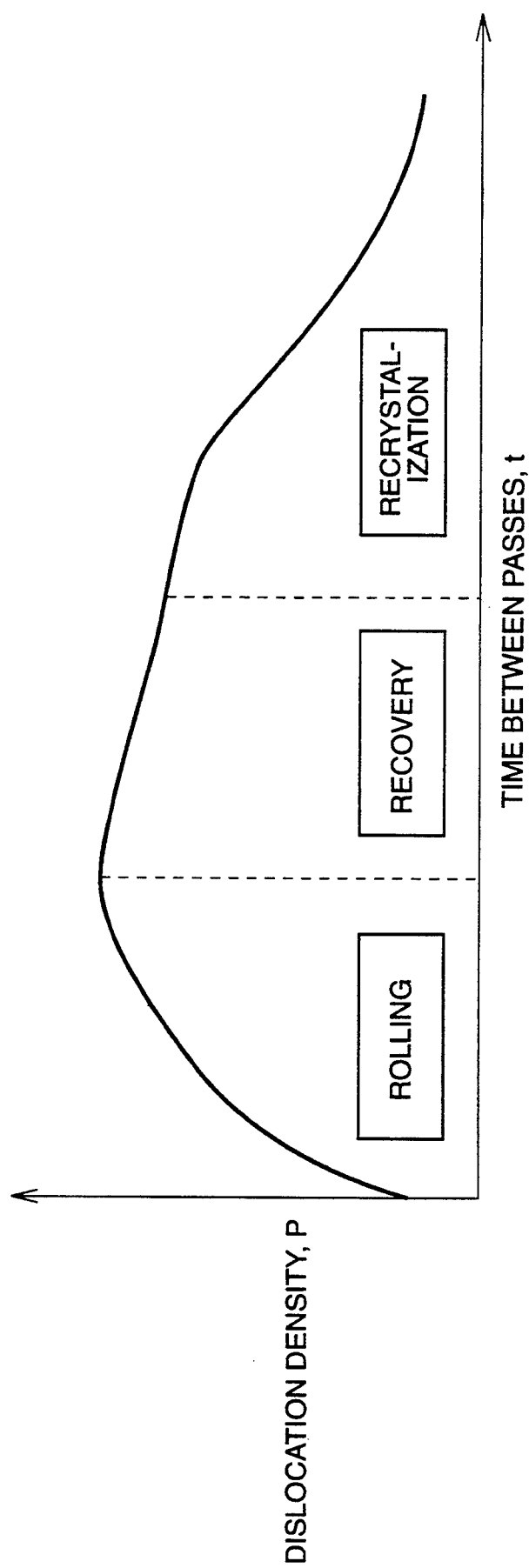
FIG. 5 is a characteristic diagram showing a change in the dislocation density during rolling.

When the steel is rolled in a plurality of passes, since the dislocation density varies between passes during the course of rolling→recovery→ recrystallization as shown in FIG. 5, a calculation for recrystallization and recovery is performed for each pass. Calculations for the austenite grain diameter, average dislocation density, etc. for each pass and after completion of rolling are performed as follows. At the outset, constant and initial values necessary for the calculation are set, and the intergranular area per unit volume of austenite after rolling is calculated.

When the draft of the rolling is large, instantaneous recrystallization, that is, dynamic recrystallization, occurs. Accordingly, it is determined whether or not dynamic recrystallization has occurred, and when the judgment is positive, the dislocation density and recrystallized grain diameter are calculated. When the dynamic recrystallization is not completed, the time taken for recrystallization to occur is then calculated and a calculation of the recovery time and static recrystallization (recrystallinity and recrystallized grain diameter) is completed.

On the other hand, when the recrystallization is completed, a calculation of the grain growth is performed and the average grain diameter of the crystal grain and the average dislocation density are further computed. This step is repeated until the final pass so as to obtain final pass information (intergranular area of austenite and dislocation density). A precipitation model, which will be described later, is computed parallel with the above step so as to add the state of solid solution and precipitation of each element during rolling to the above-described computation conditions for a rolled structure.

Figure 6:
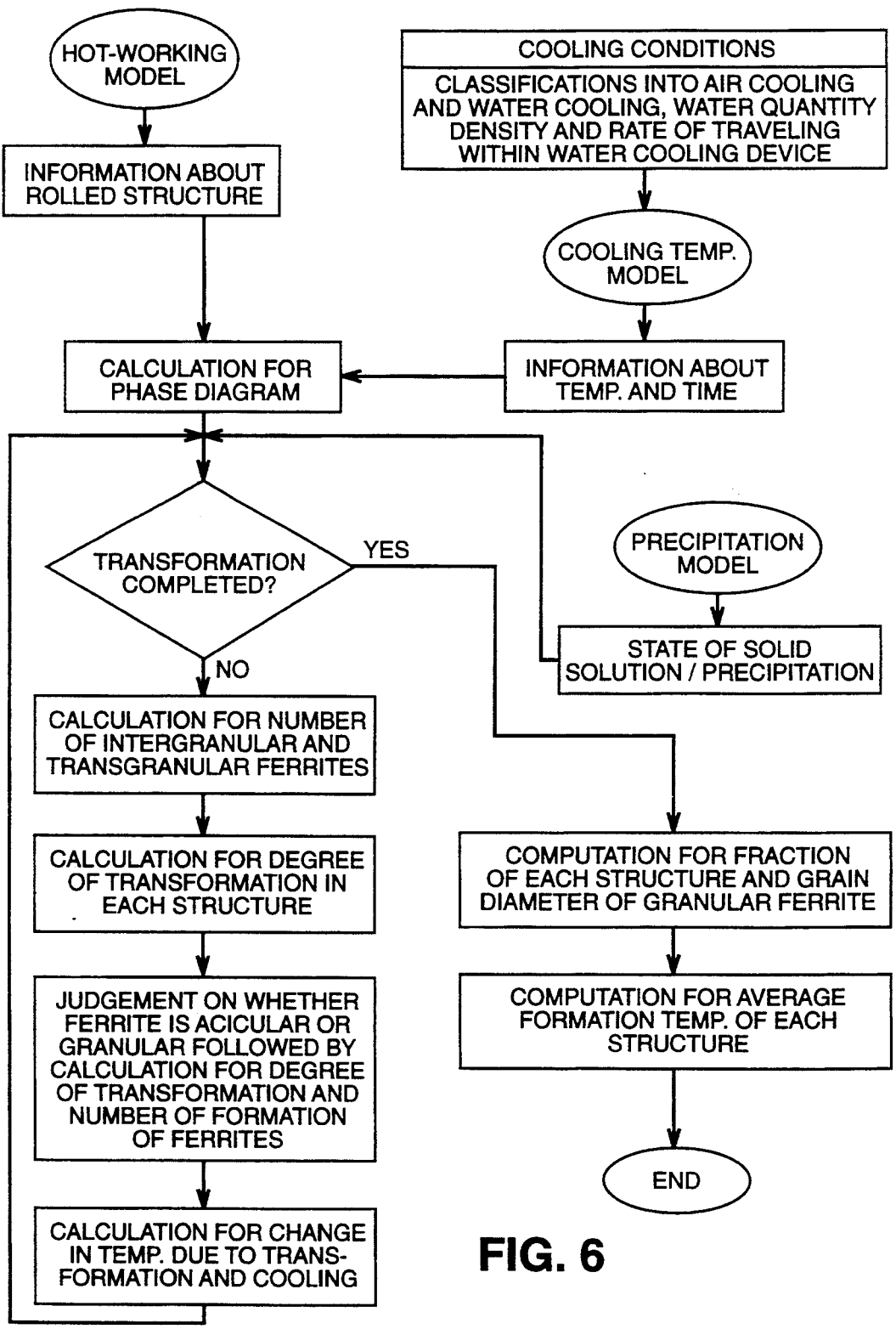
FIG. 6 is a diagram showing a construction and a computing flow of a transformation model.

FIG. 6 is a diagram showing a construction and a computing flow of a transformation model.

In this model, information concerning a steel product or a slab, such as ingredients and size, the results of a computation of the model in the previous model or arbitrarily assumed conditions corresponding to the model and cooling conditions are input. The previous step includes, besides rolling and reheating, the above-described cooling step during casting. The cooling conditions include a classification into air cooling and water cooling, a water quantity density within a cooling device and a travel rate of the steel product, etc. The forced cooling is not limited to water cooling, and cooling with a molten salt, which is a future promising means, can be applied if a physical constant, such as a heat transfer coefficient, is set.

In the computation step, at the outset, the thermal history during cooling is computed from a cooling temperature model based on the above-described input items, and, at the same time, the state of a solid solution and precipitation during cooling is computed from a precipitation model.

The transformation behavior of the steel is influenced by the state of austenite (the austenite grain diameter or intergranular area per unit volume, the residual dislocation density and the state of the solid solution and precipitation of a precipitate) before transformation and the cooling rate. In the present model, a calculation is performed based on the above-described input items for the advance of transformation, the fractions of individual structures such as intergranular ferrite, transgranular ferrite, pearlite, bainite and martensite and further the grain diameter and fraction when the ferrite is granular.

The calculation method is as follows.

At the outset, a calculation for a phase diagram of the ingredients is performed, and conditions (temperature region) under which individual structures are thermodynamically formed are determined. Then, with respect to a structure that has been judged to be formable, an increment of the degree of transformation within a given small period of time is determined, while with respect to ferrite, an increment of the number of formed grains in this period of time is determined.

Further, when ferrite is formed, it is determined whether the shape is acicular or granular. When the shape is granular, the number of formed grains and the increment of the degree of transformation are regarded respectively as the increment of the number of ferrite grains and the increment of the amount of granular ferrite. On the other hand, when the shape is acicular, only the increment of the degree of transformation is determined. A temperature change according to the degree of transformation is then calculated for the purpose of conducting a feedback of the generation of heat accompanying the transformation as cooling temperature information. Temperature changes are also fed back to the parallel precipitation model for use in the computation for the state of solid solution and precipitation during cooling.

The above-described calculation is repeated until the cooling (transformation) is completed, and the fractions of respective final structures and the grain diameter of granular ferrite are determined from the fraction and the number of grains by adding the increment of the degree of transformation and the increment of the number of granular ferrite grains. Further, the average temperature, at which each of ferrite, pearlite, bainite, martensite, etc. is formed, (average formation temperature), is calculated based on the degree of transformation and the temperature change corresponding to the degree of transformation.

In the above-described calculation, the ferrite is classified into granular ferrite and acicular ferrite for the purpose of estimating the properties of the steel product with a high degree of accuracy. This classification derives from the fact that shapes, such as granular and acicular shapes, participate in the properties of the steel product. The information concerning the average formation temperature is necessary because the properties of the steel product varies depending upon the formation temperature. It is used in the structure/property model etc. which will be described later.

The homogeneous diffusion heat treatment model, preliminary rolling model, quenching model, tempering model and normalizing model will now be described. These models each comprise a combination of the above-described heating model, hot rolling model, transformation model, etc.

The homogeneous diffusion heat treatment model comprises a heating model and a transformation model.

In this model, initial conditions, i.e., information concerning steel ingredients, slab size, information about a metallic structure, information about segregation, information about solid solution and precipitation, and further heating and cooling conditions for the homogeneous diffusion heat treatment such as the heating furnace atmosphere temperature, the period of time in the furnace and the classification of cooling after withdrawal from the furnace are input. The results of the computation for the casting model, which is a general previous step, constitute the initial condition. It is also possible to provide arbitrarily assumed initial conditions, which enables the computation time to be shortened.

The preliminary rolling model comprises the heating model, hot rolling model and transformation model.

The initial condition comprises the results of a computation of the previous step, for example, a model corresponding to a casting or homogeneous diffusion heat treatment or an arbitrarily assumed state of a metallic structure corresponding thereto. In this model, the above-described initial conditions, information concerning solid solution and precipitation, reheating conditions in the preliminary rolling, rolling conditions and cooling conditions are input.

The quenching model comprises the above-described heating model and transformation model, which apply identical computation means.

The initial condition is the state of the metallic structure passing through a rolling-cooling step, and comprises the results of a computation of a model or an arbitrarily assumed state. In this model, the above-described initial conditions and information concerning the steel product, such as ingredients and size, information concerning solid solution and precipitation and the conditions for reheating and cooling in the quenching step are input.

The tempering model consists of the above-described heating model alone, and the temperature region is limited to Acl or less.

The initial condition is the state of a metallic structure passed through a rolling-cooling step or a rolling-cooling step and a quenching step and comprises the results of a computation of a model or an arbitrarily assumed state. In this model, the above-described initial conditions and information concerning a steel product, such as ingredients and size, information concerning a solid solution and precipitation and the reheating and cooling conditions in the tempering step are input.

A precipitation model as well is parallel computed according to the computed thermal history based on the above-described input items for conducting a computation for the decomposition/formation of a metallic structure and the state of a carbide/precipitate.

The normalizing model comprises the above-described heating model and transformation model and is fundamentally applied using by the same computation means as that of the quenching model.

The initial condition is the state of a metallic structure passed through the rolling-cooling step, and the state of a metallic structure comprises the results of a computation of a model or an arbitrarily assumed state. In this model, the above-described initial conditions, information concerning ingredients and size and the reheating and cooling conditions in the normalizing step are input.

In the precipitation model wherein the state of the solid solution and precipitation of elements throughout the above-described individual steps is computed, the state of the solid solution and precipitation of each element is computed from various information (including the state of solid solution and precipitation) in the step previous to an intended step and the conditions for the intended step. This precipitation model is always computed parallel to each above-described model and successively utilized in the computation of each model, and the results (information about a metallic structure) are fed back to the precipitation model.

Figure 7:
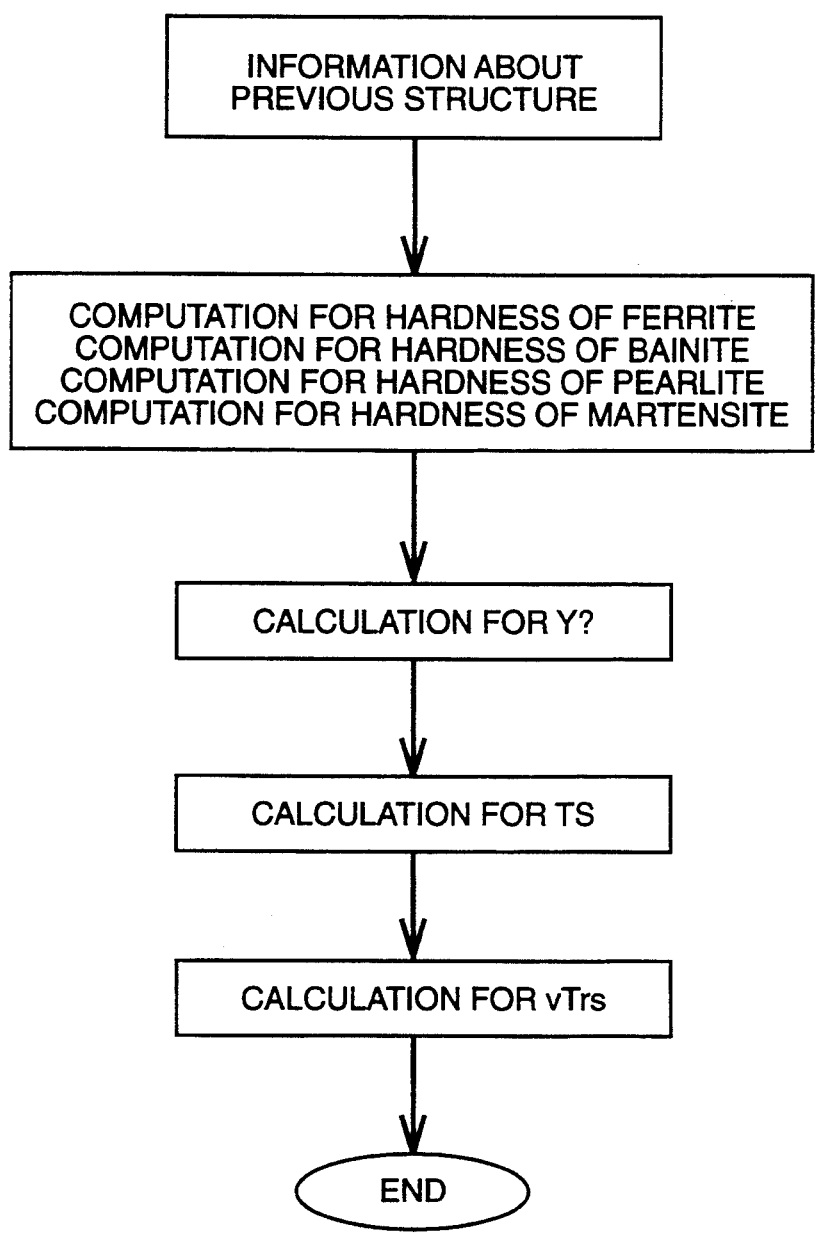
FIG. 7 is a diagram showing a construction and a computing flow of a structure-property model.

FIG. 7 is a diagram showing a construction and a computing flow of a structure-property model.

The object of the structure-property model is to compute the yield strength (YP), tensile strength (TS) and ductile/brittle fracture transition temperature (vTrs) in the V Charpy impact test using a combination of the above-described individual models corresponding to the steel product production steps. In this model, the results of a computation of a model corresponding to the final step, through which the steel product has passed, are input.

At the outset, a calculation for the hardness of individual structures (ferrite, pearlite, bainite, martensite, etc.) and a calculation for the yield strength are conducted based on the above-described input items. The tensile strength is then calculated using the calculated hardness value. Further, the ductile/brittle fracture transition temperature in the V Charpy impact test is calculated to finish the processing.

As with all of the above-described models, the present model can be solely computed. In this case, the ferrite grain diameter and measured values or arbitrarily assumed values of the fraction/hardness of each structure may be input to compute the properties of the steel product.

When the above-described series of computations are conducted, it becomes possible to automatically estimate the properties of the steel product. The results are stored in a recording medium such as a floppy disk and printed by means of a printer.

The divided time intervals, the number of steel sheet divisions in the sheet direction, etc. for conducting a computation for information concerning the structure and the solid solution and precipitation can be set according to the purpose, which contributes to an improvement in computation accuracy and shortening of computing speed and enables information concerning the structure and properties deviation in the sheet thickness direction to be obtained.

TEST EXAMPLE

Figure 8:
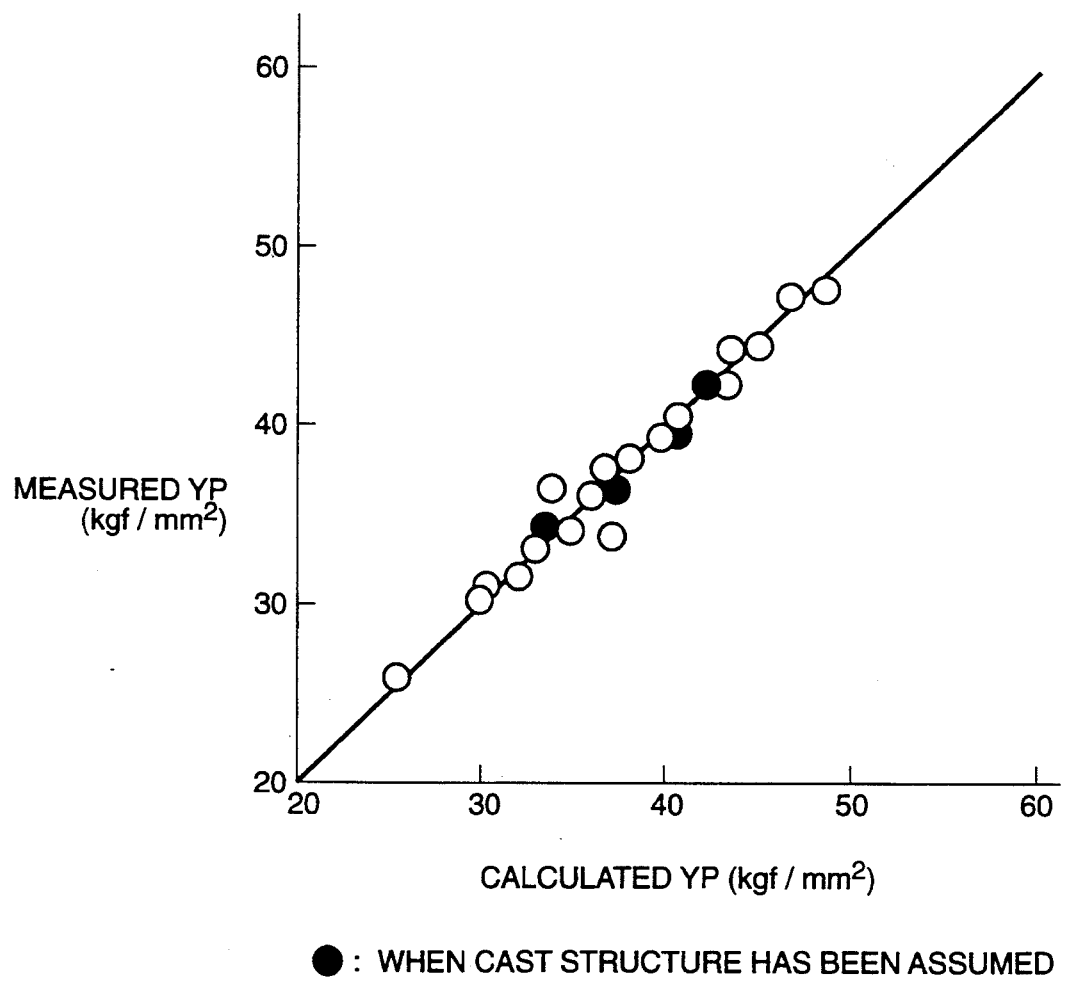
FIG. 8 is a diagram showing a comparison of the measured value with the value calculated according to the method of the present invention with respect to the yield strength.
Figure 9:
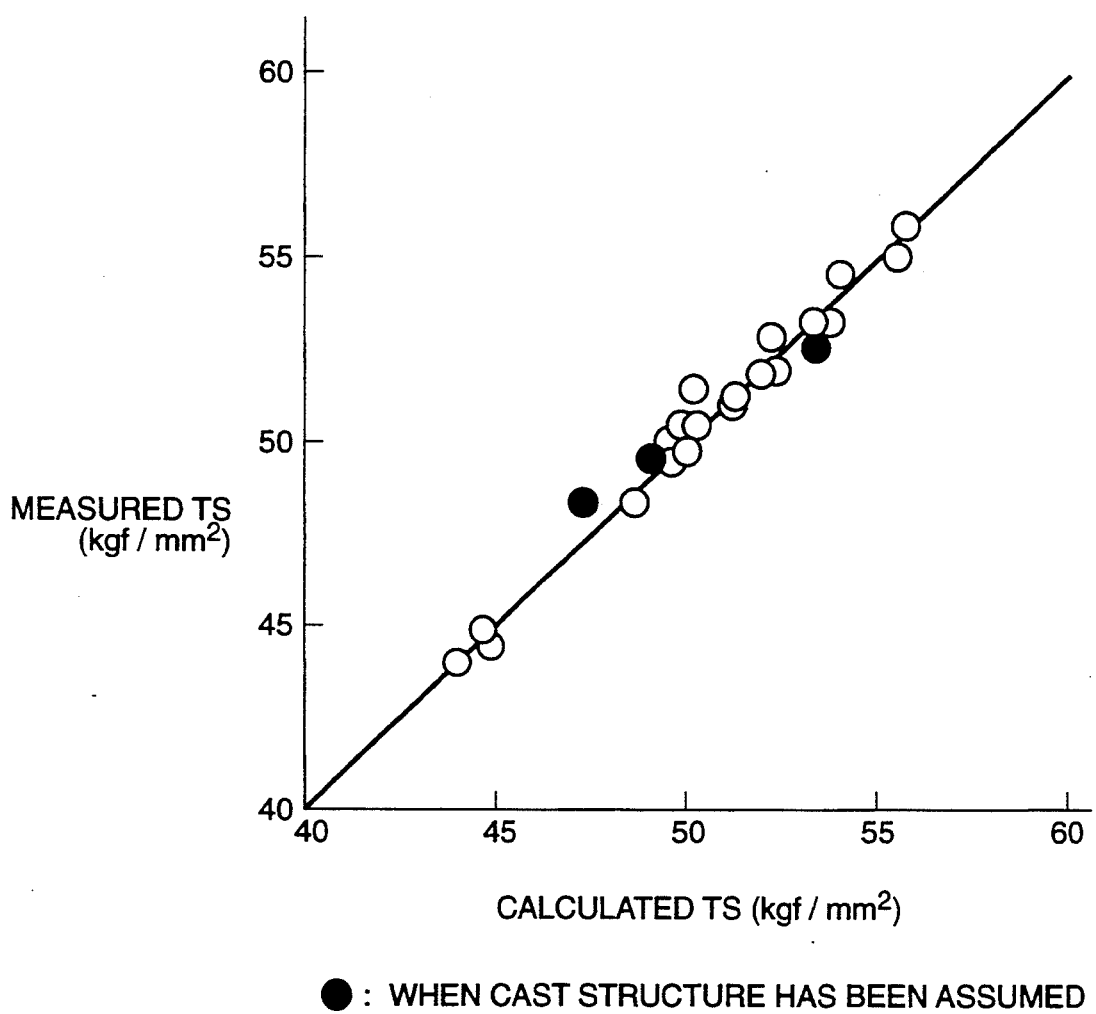
FIG. 9 is a diagram showing a comparison of the measured value with the value calculated according to the method of the present invention with respect to the tensile strength.
Figure 10:
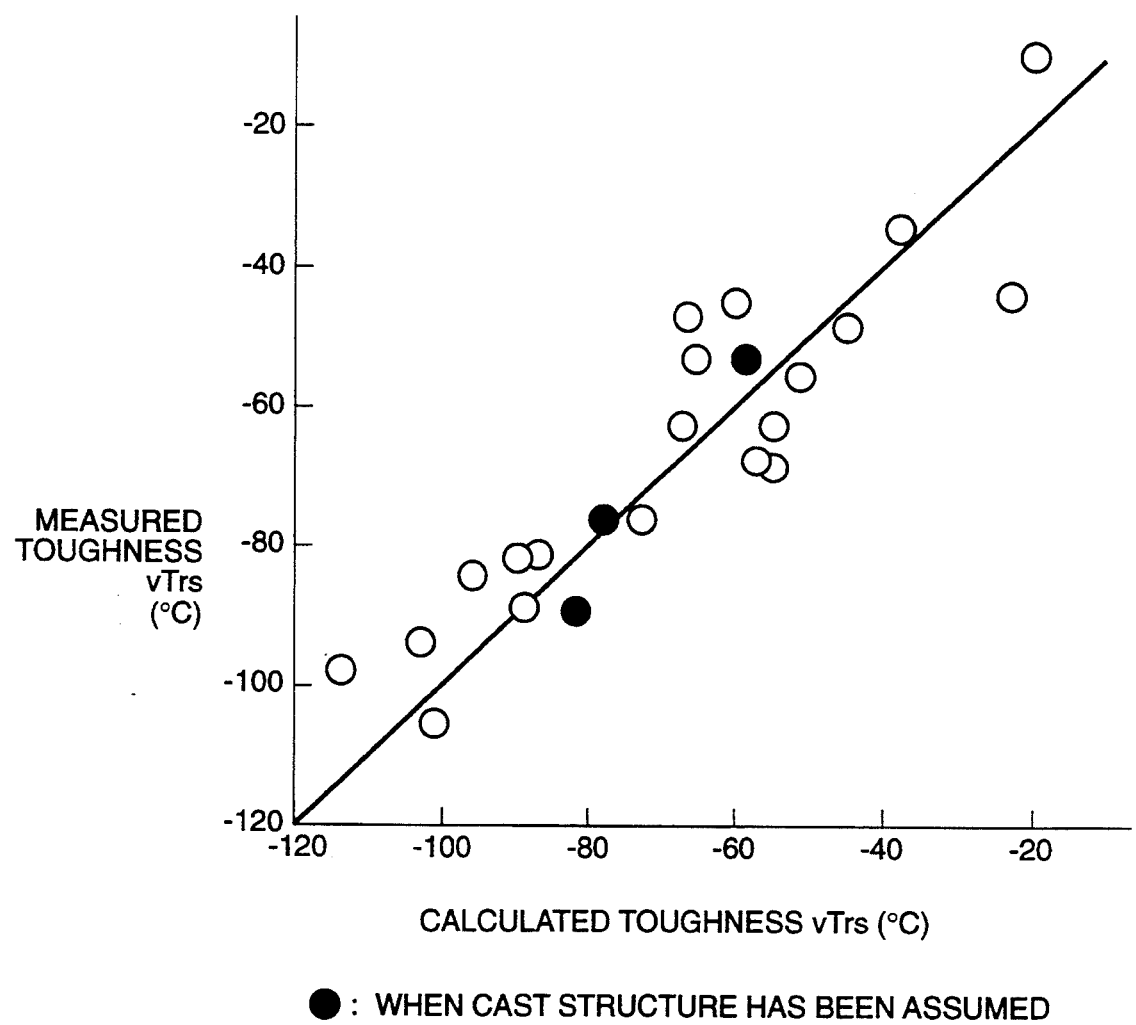
FIG. 10 is a diagram showing a comparison of the measured value with the value calculated according to the method of the present invention with respect to the ductile/brittle fracture transition temperature (vTrs) in a V Charpy impact test.

Table 1 shows chemical ingredients of a steel applied to the present invention, Table 2 shows production steps, and FIGS. 8 to 10 each show a comparison of measured values of yield strength (YP), tensile strength (TS) and the ductile/brittle fracture transition temperature (vTrs) in a V Charpy impact test with calculated values determined by the above-described estimation method.

As is apparent from FIGS. 8 to 10, the measured values are close to the calculated values, which substantiates that the estimation could be made with a very high degree of accuracy. Further, in Table 2, in the case of steels A-6, A-7 and A-8, a calculation wherein the cast structure is assumed without a computation for the cast model is also performed. The results are indicated by a black dot ( ● ) in FIGS. 8 to 10. In this case as well, the estimation accuracy is comparable to that of the above-described case and on a level satisfactory for practical use. When the cast model is not computed, the total computation time can be shortened and in the present test example, a shortening of about 25% can be attained.

Thus, since a highly reliable estimation is possible, it is also possible to perform a computation for production conditions of a product according to the properties required by users.

TABLE 2

| Steel | Casting | SP[1] | BD[2] | Reheating | Rolling | Cooling | Q[3] | T[4] | N[5] |
|-------|---------|-------|-------|-----------|---------|---------|------|------|------|
| A-1 | ○ | | | | ○ | ○ | | | |
| A-2 | ○ | | | | ○ | ○ | | | |
| A-3 | ○ | | | | ○ | ○ | ○ | ○ | |
| A-4 | ○ | | | | ○ | ○ | | | ○ |
| A-5 | ○ | | | ○ | ○ | ○ | | | |
| A-6 | ○* | | | | ○ | ○ | | ○ | |
| A-7 | ○* | | | | ○ | ○ | ○ | ○ | |
| A-8 | ○* | | | | ○ | ○ | | | ○ |
| B-1 | ○ | ○ | | | ○ | ○ | | | |
| B-2 | ○ | ○ | | | ○ | ○ | | ○ | |
| B-3 | ○ | ○ | | | ○ | ○ | ○ | ○ | |
| B-4 | ○ | ○ | | | ○ | ○ | | | ○ |
| C-1 | ○ | | ○ | ○ | ○ | ○ | | | |
| C-2 | ○ | ○ | | ○ | ○ | ○ | | ○ | |
| C-3 | ○ | | ○ | ○ | ○ | ○ | ○ | ○ | |
| C-4 | ○ | ○ | | ○ | ○ | ○ | | | ○ |
| C-5 | ○ | | | ○ | ○ | ○ | | | |
| C-6 | ○ | | | ○ | ○ | ○ | | | |
| C-7 | ○ | | | ○ | ○ | ○ | ○ | ○ | |
| C-8 | ○ | | | ○ | ○ | ○ | | | ○ |

Note:
[1]homogeneous diffusion heat treatment, [2]preliminary rolling, [3]quenching, [4]tempering, [5]normalizing,
*Integrated calculation was also practiced, assuming the casting structure.

EFFECT OF THE INVENTION

The present invention has the following effects because in each step of casting for steel making (a continuous casting process or a steel ingot process), a treatment (a homogeneous diffusion treatment or preliminary rolling) of a slab (a steel ingot), reheating of a slab (a steel ingot), rolling, cooling (air cooling and forced cooling), a heat treatment (quenching, tempering or normalizing), which are steps for producing a hot rolled steel product, an index for a steel product property in each step is computed from the conditions in the step, steel ingredients, size, etc., and the properties of the steel product are estimated from information concerning the metallic structure, information concerning the solid solution and precipitation (amount and size), etc. in the final step.

(1) As opposed to the prior art, testing and measuring a finished product can be significantly simplified or rendered unnecessary.

(2) Production conditions capable of satisfying quality requirements can be set at the stage of production.

(3) It has become possible to conduct the estimation and control of the properties of the steel product wherein the properties are estimated in each step during the production and the process conditions are controlled so that the quality requirements are satisfied.

(4) The properties of the steel product can be estimated by providing conditions assumed in the development of a novel steel product and a novel process, which significantly reduces the burden

TABLE 1

| | | | | | | | | | | (wt. %, *: ppm) | |
|---|---|---|---|---|---|---|---|---|---|---|---|
| Steel | C | Si | Mn | P | S | Al | Cu | Ni | Cr | Mo | Nb |
| A | 0.07 | 0.17 | 0.91 | 0.011 | 0.004 | 0.024 | 0.22 | 0.15 | | 0.54 | |
| B | 0.13 | 0.25 | 1.24 | 0.016 | 0.004 | 0.022 | | | 0.13 | | 0.021 |
| C | 0.05 | 0.28 | 1.40 | 0.007 | 0.001 | 0.020 | 0.04 | | | 0.23 | 0.008 |

| Steel | V | Ti | Ta | B | W | Co | Ca | Rem | N* | O* |
|-------|---|----|----|---|---|----|----|-----|----|----|
| A | 0.035 | 0.011 | | 0.0005 | | | 0.0021 | 0.0007 | 26 | 30 |
| B | | | | | | | 0.0035 | | 33 | 31 |
| C | | 0.013 | 0.005 | | 0.0006 | 0.012 | | | 28 | 26 | and development time of the novel steel product and process.

UTILIZATION IN INDUSTRY

As described above, the method of estimating the properties of a steel product according to the present invention can be widely applied to a steel plate, a hot coil, a shape steel, etc. in the steel industry. Further, the use of a method for estimating the properties of a steel product according to the present invention can facilitate properties and process control and the design of ingredients with a high degree of accuracy.

We claim:

1. A method of estimating, based on steel ingredients and production conditions, the properties of a steel product produced by subjecting a slab cast according to a continuous casting process or an ingot making process to at least rolling and cooling, comprising the steps of:

computing the temperature of a slab based on casting conditions including at least slab size, drawing rate and cooling water quantity density and time wherein said steel slab has a metallic structure after casting including an equi-axed crystal and columnar crystal fraction, and equi-axed and columnar austenite grains having a diameter, and further completing a computation for the state of the metallic structure after casting including at least the fraction of equi-axed crystal and columnar crystal, the diameter of equi-axed and columnar austenite grains, the state of solid solution and precipitation and the state and concentration of segregation;

completing a computation for determining the state of the metallic structure after rolling including at least the diameter of an austenite grain, the intergranular area of austenite per unit volume, the dislocation density within austenite and the state of solid solution and precipitation based on the state of the metallic structure before the rolling and the temperature of the steel product computed from rolling conditions including at least the size of the steel product on input and output sides in each pass anti the period of time between passes;

completing a computation for determining the state of the metallic structure after cooling including at least the fraction of each structure of ferrite, pearlite, bainite and martensite, the grain diameter of ferrite and the state of solid solution and precipitation based on the state of the metallic structure before cooling and the temperature of the steel product computed from cooling conditions including at least classification into water cooling and air cooling and the water quantity density and travel rate within a device; and when the steel product has a final state metallic structure, completing a computation for determining the properties of the steel product based on the final state of the metallic structure.

2. The method according to claim 1, which further comprises, in order to cope with optional reheating conducted prior to rolling, said reheating occurring in a furnace having an atmosphere, said atmosphere having a temperature, the step of completing a computation for determining the state of the metallic structure after reheating including at least the grain diameter of austenite and the state of solid solution and precipitation based on the state of the metallic structure before reheating and the temperature of the slab computed from reheating conditions, including at least the furnace atmosphere temperature and the period of time in the furnace.

3. The method according to claim 2, which further comprises, in order to cope with a homogeneous diffusion heat treatment conducted optionally subsequent to casting, the step of completing a computation for determining the state of the metallic structure after the homogeneous diffusion heat treatment including at least the state of solid solution and precipitation of each element and the state and concentration of segregation based on the state of the metallic structure after casting and homogeneous diffusion treatment conditions including at least the furnace atmosphere temperature, the period of time in the furnace and cooling conditions after withdrawal from the furnace.

4. The method according to claim 3, which further comprises, in order to cope with preliminary rolling conducted optionally subsequent to the homogeneous diffusion heat treatment, the step of completing a computation for determining the state of the metallic structure after the preliminary rolling including at least the state of solid solution and precipitation of each element and the state and concentration of segregation by using, as all initial condition, the state of the metallic structure after the homogeneous diffusion heat treatment, said step comprising the substeps of:

completing a computation for determining the state of the metallic structure after reheating in the preliminary rolling including at least the grain diameter of austenite and the state of solid solution and precipitation of each element based on the state of the metallic structure before the reheating in the preliminary rolling and the slab temperature computed from reheating conditions including the furnace atmosphere temperature and the period of time in the furnace;

completing a computation for determining the state of the metallic structure after the rolling in the preliminary rolling including at least the grain diameter of austenite, the dislocation density within austenite and the state of solid solution and precipitation based on the state of the metallic structure before the rolling in the preliminary rolling and the temperature of the steel product computed from rolling conditions including at least the size of the steel product on inlet and outlet sides in each pass and the period of time between passes, and completing a computation for determining the state of the metallic structure after cooling including at least the fraction of each structure of ferrite, pearlite, bainite and martensite, the grain diameter of ferrite and the state of solid solution and precipitation based on the state of the metallic structure before the cooling in the preliminary rolling and the temperature of the steel product computed from cooling conditions including at least the classification into water cooling and air cooling and the water quantity density and travel rate within a cooling device.

5. The method according to claim 2, which further comprises, in order to cope with the preliminary rolling conducted optionally subsequent to the casting, the step of completing a computation for determining the state of the metallic structure after the preliminary rolling including at least the state of solid solution and precipitation of each element and the state and concentration of segregation, the fraction of the structure and the grain diameter of ferrite by using, as an initial condition, the state of the metallic structure after the casting; said step comprising the substeps of:

completing a computation for determining the state of the metallic structure after reheating in the preliminary rolling including at least the grain diameter of austenite and the state of solid solution and precipitation of each element based on the state of the metallic structure before the reheating in the preliminary rolling and the slab temperature computed from reheating conditions including at least the furnace atmosphere temperature and the period of time in the furnace;

completing a computation for determining the state of the metallic structure after rolling in the preliminary rolling including at least the grain diameter of austenite, the dislocation density within austenite and the state of solid solution and precipitation based on the state of the metallic structure before the rolling in the preliminary rolling and the temperature of the steel product computed from rolling conditions including at least the size of the steel product on inlet and outlet sides in each pass and the period of time between passes, and completing a computation for determining the state of the metallic structure after cooling in the preliminary rolling including at least the fraction of each structure of ferrite, pearlite, bainite and martensite, the grain diameter of ferrite and the state of solid solution and precipitation based on the state of the metallic structure before cooling in the preliminary rolling and the temperature of the steel product computed from cooling conditions including at least classification into water cooling and air cooling and the water quantity density and travel rate within a cooling device.

6. The method according to claim 1 which further comprises, in order to cope with tempering conducted optionally subsequent to the cooling, the step of completing a computation for determining the state of the metallic structure after tempering including at least the fraction of each structure of ferrite, pearlite, bainite and martensite, the grain diameter of ferrite and the amount and size of a precipitate and the state of solid solution based on the state of the metallic structure before the tempering and tempering conditions including at least heating and cooling conditions.

7. The method according to claim 6, which further comprises, in order to cope with quenching conducted optionally prior to the tempering, the step of completing a computation for determining the state of the metallic structure after quenching including at least the state of solid solution and precipitation, the fraction of each structure of ferrite, pearlite, bainite and martensite and the grain diameter of ferrite based on the state of the metallic structure after the cooling and quenching conditions including at least heating and cooling conditions.

8. The method according to claim 1 which further comprises, in order to cope with normalizing conducted optionally subsequent to the cooling, the step of completing a computation for determining the state of the metallic structure after normalizing including at least the state of solid solution and precipitation, the fraction of each structure of ferrite, pearlite, bainite and martensite and the grain diameter of ferrite based on the state of the metallic structure after the cooling and normalizing conditions including at least heating and cooling conditions.

9. A method of estimating, based on steel ingredients and production conditions, fine quality of a steel product produced by subjecting a slab cast according to a continuous casting process or an ingot making process to at least reheating, rolling, cooling and tempering, the steel having a metallic structure state after each processing step, comprising the steps of:

completing a computation for determining the state of the metallic structure after rolling including at least the grain diameter of austenite, the intergranular area of austenite per unit volume, the dislocation density in austenite and the state of solid solution and precipitation based on the state of the metallic structure before the rolling and the temperature of the steel product computed from rolling conditions including at least the size of the steel product on inlet and outlet sides in each pass and the period of time between passes;

completing a computation for determining the state of the metallic structure after cooling including at least the fraction of each structure of ferrite, pearlite, bainite and martensite, the grain diameter of ferrite and the state of solid solution and precipitation based on the state of the metallic structure before the cooling and the temperature of the steel product computed from cooling conditions including at least classification into water cooling and air cooling and the water quantity density and the travel rate within device;

completing a computation for determining the state of the metallic structure after tempering including at least the fraction of each structure of ferrite, pearlite, bainite and martensite based on the state of the metallic structure before the tempering and tempering conditions including at least heating and cooling conditions; and when the steel product has a final metallic structure state, completing a computation for determining the properties of the steel product based on the final state of the metallic structure.

10. The method according to claim 9, which further comprises, in order to cope with quenching conducted optionally prior to the tempering, completing a computation for determining the state of the metallic structure after quenching including at least the state of solid solution and precipitation, the fraction of each structure of ferrite, pearlite, bainite and martensite and the grain diameter of ferrite based on the state of the metallic structure after cooling and the quenching conditions including at least heating and cooling conditions.

11. A method of estimating, based on steel ingredients and production conditions, the properties of a steel product produced by subjecting a slab cast according to a continuous casting princess or an ingot making process to reheating, rolling, cooling and normalizing, comprising the steps of:

completing a computation for determining the state of a metallic structure after rolling including at least the grain diameter of austenite, the intergranular area of austenite per unit volume, the dislocation density in austenite and the state of solid solution and precipitation based on the state of the metallic structure before the rolling and the temperature of the steel product computed from rolling conditions including at least the size of the steel product on inlet and outlet sides in each pass and the period of time between passes;

completing a computation for determining the state of the metallic structure after cooling including at least the fraction of each structure of ferrite, pearlite, bainite and martensite, the grain diameter of ferrite and the state of solid solution and precipitation based on the state of the metallic structure before the cooling and the temperature of the steel computed from cooling conditions including at least classification into water cooling and air cooling and the water quantity density and the travel rate within a cooling device;

completing a computation for determining the state of the metallic structure after normalizing including at least the state of solid solution and precipitation, the fraction of each structure of ferrite, pearlite, bainite and martensite based on the state of the metallic structure after cooling and the normalizing conditions including at least heating and cooling conditions; and when the steel product has a final metallic structure state, completing a computation for determining the properties of the steel product based on the final state of the metallic structure.

* * * * *

UNITED STATES PATENT AND TRADEMARK OFFICE
CERTIFICATE OF CORRECTION

PATENT NO. : 5,357,443
DATED : October 18, 1994
INVENTOR(S) : Yoshiyuki WATANABE, et al.

It is certified that error appears in the above-indentified patent and that said Letters Patent is hereby corrected as shown below:

Column 3, line 11, delete the period after "slab".

Column 12, line 28, change "all" to --an--.

Column 12, line 65, delete "the" before "preliminary".

Column 14, line 11, change "fine" to --the--.

Column 14, line 38, before "device;" insert --a cooling--.

Signed and Sealed this

Fourteenth Day of March, 1995

Attest:

BRUCE LEHMAN

*Attesting Officer*          *Commissioner of Patents and Trademarks*